US00PP29791P3

(12) United States Plant Patent
Grosser

(10) Patent No.: US PP29,791 P3
(45) Date of Patent: Nov. 6, 2018

(54) SWEET ORANGE TREE NAMED 'FLORIDA EV1'

(50) Latin Name: *Citrus sinensis*
Varietal Denomination: Florida EV1

(71) Applicant: Florida Foundation Seed Producers, Inc., Marianna, FL (US)

(72) Inventor: Jude W. Grosser, Winter Haven, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 275 days.

(21) Appl. No.: 14/998,502

(22) Filed: Jan. 13, 2016

(65) Prior Publication Data

US 2017/0202121 P1 Jul. 13, 2017

(51) Int. Cl.
*A01H 5/08* (2018.01)

(52) U.S. Cl.
USPC ..... Plt./202
CPC ..... *A01H 5/0806* (2013.01)

(58) Field of Classification Search
USPC ..... Plt./202, 201
CPC ..... A01H 5/0806
See application file for complete search history.

(56) References Cited

U.S. PATENT DOCUMENTS

| | | | |
|---|---|---|---|
| PP21,535 | P2 | 11/2010 | Grosser et al. |
| PP26,087 | P3 | 11/2015 | Grosser |
| 2016/0120083 | P1 | 4/2016 | Grosser |
| 2016/0128252 | P1 | 5/2016 | Grosser |
| 2016/0128253 | P1 | 5/2016 | Grosser |

OTHER PUBLICATIONS

Citrus, UF University of Florida IFAS 2017, 2 pages. (http://research.ifas.ufl.edu/media/researchifasufledu/docs/pdf/Citrus.pdf).*
U.S. Appl. No. 14/998,531, filed Jan. 13, 2016, Grosser.
Grosser et al., "Protoplast fusion and citrus improvement," *Plant Breeding Reviews* 8:339-374, 1990.
Larkin et al., "Somaclonal variation—a novel source of variability from cell cultures for plant improvement," *Theoretical and Applied Genetics* 60:197-214, 1981.
Grosser et al., Somaclonal Variation in Sweet Orange: Practical Applications for Variety Improvement and Possible Causes. pp. 219-234. IN: Kahn, I.H. (Ed.). Citrus Genetics, Breeding and Biotechnology. CAB International. 2007.

* cited by examiner

*Primary Examiner* — Kent L Bell
(74) *Attorney, Agent, or Firm* — Dentons US LLP

(57) ABSTRACT

The new and distinct sweet orange tree described herein originated as a 'Valencia' somaclone tree regenerated from an adventitious bud developed on a nucellar seedling stem piece. 'Florida EV1' is a true 'Valencia' sweet orange with an altered maturity date that allows for harvest 8-12 weeks earlier than traditional 'Valencia' trees.

3 Drawing Sheets

Latin name of the genus and species of the plant claimed: *Citrus sinensis*.
Variety denomination: 'Florida EV1'.

BACKGROUND OF THE INVENTION

The present invention relates to a new and distinct variety of sweet orange named 'Florida EV1'. 'Florida EV1' originated as a 'Valencia' somaclone tree regenerated from an adventitious bud developed on a nucellar seedling stem piece induced using tissue culture techniques from standard 'Valencia' (*Citrus sinensis* L. Osbeck) in 1989. Somaclonal variation is defined as variability in plants regenerated from tissue culture that is either induced or uncovered by a tissue culture process. Most somaclonal variation is negative, but if enough plants are examined, positive changes can usually be recovered. Somaclonal variation has been a primary source of genetic variation in sweet orange exploited in *citrus* improvement programs.

The first asexual reproduction of 'Florida EV1' involved grafting of the original tree to 'Carrizo' citrange rootstock and planting in Martin County, Fla. in 1989. Thus, 'Florida EV1' is a true 'Valencia' sweet orange with an altered maturity date that allows for harvest 8-12 weeks earlier than traditional 'Valencia' trees.

SUMMARY OF THE INVENTION

The new and distinct variety of sweet orange bears fruit that ripens from December through January in central Florida. The trees usually bloom between early to late March in central Florida, depending on the season. 'Florida EV1' trees are less upright and of slightly lower vigor than 'SF14W-62' and standard 'Valencia'. Second and third generation trees are less thorny than 'SF14W-62', and more similar to traditional 'Valencia' selections. Over the past two seasons, 'Florida EV1' has matured significantly earlier than the early-maturing 'SF14W-62'. 'Florida EV1' trees bear fruit that is typical of 'Valencia', although 'Florida EV1' fruit ripen 8-12 weeks earlier than standard 'Valencia' trees, based on the brix/acid ratio (Tables 1-3). Juice data from the original tree did not show that 'Florida EV1' matures earlier than 'SF14W-62', however, fruit on propagated trees have exhibited earlier maturity over the past two seasons. 'Florida EV1' appears to be slightly earlier than the partner tree, 'Florida EV2' (Co-pending U.S. Plant patent application Ser. No. 14/998,531). Juice quality of 'Florida EV1' is typical of 'Valencia' in sugar and acid content, color, and flavor. The fruit are juicy and difficult to peel. Fruit are slightly more seedy than standard 'Valencia', with 9-10 seeds per fruit (standard 'Valencia' has 4-5 seeds per fruit). The tree appears to be at least as productive as standard 'Valencia' trees.

The following are the most outstanding and distinguishing characteristics of 'Florida EV1' when grown under normal horticultural practices in Florida. (1) Fruit ripen 8-12 weeks earlier than standard 'Valencia'; (2) Fruit have excellent juice quality; and (3) Trees of 'Florida EV1' exhibit a less vigorous growth habit, which should facilitate use in Advanced *Citrus* Production Systems that feature high density plantings.

'Florida EV1' produces standard Valencia-type sweet orange fruit, but with a significantly earlier fruit maturation date (8-12 weeks) than standard 'Valencia' (Tables 1-3). In Florida, fruit can generally be harvested from December through January, depending on environmental conditions. As shown in Table 3, for the 2014-2015 juice season, fruit from 6-year-old trees on rough lemon rootstock produced juice with a brix/acid ratio of 16, whereas 'Hamlin' fruit from the same block produced juice with a brix/acid percent ratio of 12. Juice quality from fruit of 'Florida EV1' was much higher than that of 'Hamlin' in December and January, and more similar to that of standard 'Valencia', the highest quality juice orange currently available, with harvest usually beginning in March. The present 'Florida EV1' selection therefore provides the processing industry with an opportunity to replace 'Hamlin', which is currently the standard early-maturing cultivar in the Florida juice industry. Replacing 'Hamlin' with new Valencia types that mature in the same window, such as 'Florida EV1', has the potential to significantly improve the flavor and color of NFC (Not From Concentrate) orange juice. Better quality juice may help offset declining orange juice consumption in the United States. In the event of January or February freeze-mandated harvests, this would allow for grade A juice recovery without the economic loss encountered with standard 'Valencia' fruit that is not fully mature at the time of harvest. 'Florida EV1' has a maturity date similar to that of Valencia somaclone 'Florida EV2', but appears to be slightly earlier. Both trees have been significantly earlier than 'SF14W-62' (U.S. Plant Pat. No. 21,535) the past two seasons.

TABLE 1

Original tree data suggesting early maturity for 'Valencia' somaclone 'Florida EV1' (Data from B-4 Trial, Martin County, Florida). Trial no longer exists.

| Date | Selection | Brix | Acid | Ratio | Lbs. solids | Juice Color* |
|---|---|---|---|---|---|---|
| Jan. 30, 2002 | Somaclone 'Florida EV1' | 12.37 | .75 | 16.49 | 6.49 | 38.1 |
| | 'Valencia' Control | 9.82 | .82 | 11.98 | 5.36 | 37.4 |
| Feb. 14, 2003 | Somaclone 'Florida EV1' | 11.15 | .82 | 13.60 | 6.07 | 36.7 |
| | 'Valencia' Control | 11.06 | .88 | 12.57 | 5.83 | 36.4 |

TABLE 2

Juice data from 5-year-old trees on rough lemon rootstock, Alligator Grove, St. Cloud, Florida.

| ANALYSIS DATE | SAMPLE ID | BRIX COR. | ACID % | RATIO |
|---|---|---|---|---|
| Jan. 14, 2014 | 'Vernia'/Rough Lemon | 11.29 | 0.73 | 15.47 |
| Jan. 14, 2014 | 'Florida EV2'/Rough Lemon | 11.68 | 0.59 | 19.80 |
| Jan. 14, 2014 | 'SF14W-62'/Rough Lemon | 10.27 | 0.72 | 14.26 |

TABLE 2-continued

Juice data from 5-year-old trees on rough lemon rootstock, Alligator Grove, St. Cloud, Florida.

| | | | | |
|---|---|---|---|---|
| Jan. 14, 2014 | 'Valencia'/Rough Lemon | 9.22 | 0.80 | 11.53 |
| Jan. 14, 2014 | 'OLL-8'/Rough Lemon | 10.78 | 1.05 | 10.27 |
| Jan. 14, 2014 | 'Florida EV1'/Rough Lemon | 10.32 | 0.51 | 20.24 |

| ANALYSIS DATE | SAMPLE ID | SINKING PULP | VIT. C (mg/100 ml) | Limonin ppm |
|---|---|---|---|---|
| Jan. 14, 2014 | 'Vernia'/Rough Lemon | 16.0 | 50.38 | 23.1 |
| Jan. 14, 2014 | 'Florida EV2'/Rough Lemon | 18.0 | 47.49 | 5.8 |
| Jan. 14, 2014 | 'SF14W-62'/Rough Lemon | 14.0 | 47.09 | 9.0 |
| Jan. 14, 2014 | 'Valencia'/Rough Lemon | 12.0 | 43.71 | 11.1 |
| Jan. 14, 2014 | 'OLL-8'/Rough Lemon | 13.0 | 50.51 | 10.7 |
| Jan. 14, 2014 | 'Florida EV1'/Rough Lemon | 16.0 | 46.27 | 4.2 |

| ANALYSIS DATE | SAMPLE ID | pH | Juice Color* | OIL % |
|---|---|---|---|---|
| Jan. 14, 2014 | 'Vernia'/Rough Lemon | 3.75 | 36.22 | 0.018 |
| Jan. 14, 2014 | 'Florida EV2'/Rough Lemon | 4.13 | 35.14 | 0.035 |
| Jan. 14, 2014 | 'SF14W-62'/Rough Lemon | 3.86 | 35.83 | 0.026 |
| Jan. 14, 2014 | 'Valencia'/Rough Lemon | 3.66 | 35.33 | 0.012 |
| Jan. 14, 2014 | 'OLL-8'/Rough Lemon | 3.52 | 36.77 | 0.015 |
| Jan. 14, 2014 | 'Florida EV1'/Rough Lemon | 4.14 | 35.00 | 0.029 |

TABLE 3

Juice data from 6-year-old trees on rough lemon rootstock, Alligator Grove, St. Cloud, Florida. Pilot-plant data from samples run on Dec. 10, 2014.

| Sample | Variety | Lbs. Juice Per Box | Acid | Total Brix |
|---|---|---|---|---|
| 1 | 'Vernia' | 53.906 | 0.87 | 11.04 |
| 2 | 'Florida EV1' | 50.913 | 0.71 | 11.30 |
| 3 | 'Hamlin' | 52.914 | 0.94 | 11.17 |
| 4 | 'SF14W-62' | 50.728 | 0.84 | 9.87 |
| 5 | 'Florida EV2' | 50.299 | 0.67 | 11.06 |
| 6 | 'Valencia' | 53.443 | 0.98 | 9.53 |

| Sample | Ratio | Fruit Ct | Lbs. Solids Per Box | Juice color* |
|---|---|---|---|---|
| 1 | 12.69 | 78 | 5.95 | 35.3 |
| 2 | 15.92 | 61 | 5.75 | 36 |
| 3 | 11.88 | 64 | 5.91 | 34.5 |
| 4 | 11.75 | 55 | 5.01 | 35.7 |
| 5 | 16.51 | 63 | 5.56 | 36 |
| 6 | 9.72 | 58 | 5.09 | 35.4 |

*Juice color, also referred to as juice color number, is an industry standard measurement of *citrus* juice color that can be obtained using a HunterLab Model D45 *Citrus* Colorimeter for which the *Citrus* Red (CR) and *Citrus* Yellow (CY) has been calibrated with USDA orange juice standard color tube No 4; USDA grade "A" orange juice requires a juice color number of at least 36. Juice color number is calculated using the following formula: 22.510+(0.165)*CR+(0.111)*CY.

BRIEF DESCRIPTION OF THE DRAWINGS

'Florida EV1' is illustrated by the accompanying photographs, which show the tree's form, foliage, and fruit. The colors shown are as true as can be reasonably obtained by conventional photographic procedures. The photographs are of a tree approximately 5 years old.

FIG. 1—Shows a close-up of the mature 'Florida EV1' Valencia fruit with the rind, and a cross-sectional view of the fruit when cut in the center.

FIG. 2—Shows mature 'Valencia' somaclone 'Florida EV1' fruits hanging on the tree in early winter.

FIG. 3—Shows a close-up of the mature 'Valencia' somaclone 'Florida EV1' fruit.

DETAILED BOTANICAL DESCRIPTION

Figure 1:
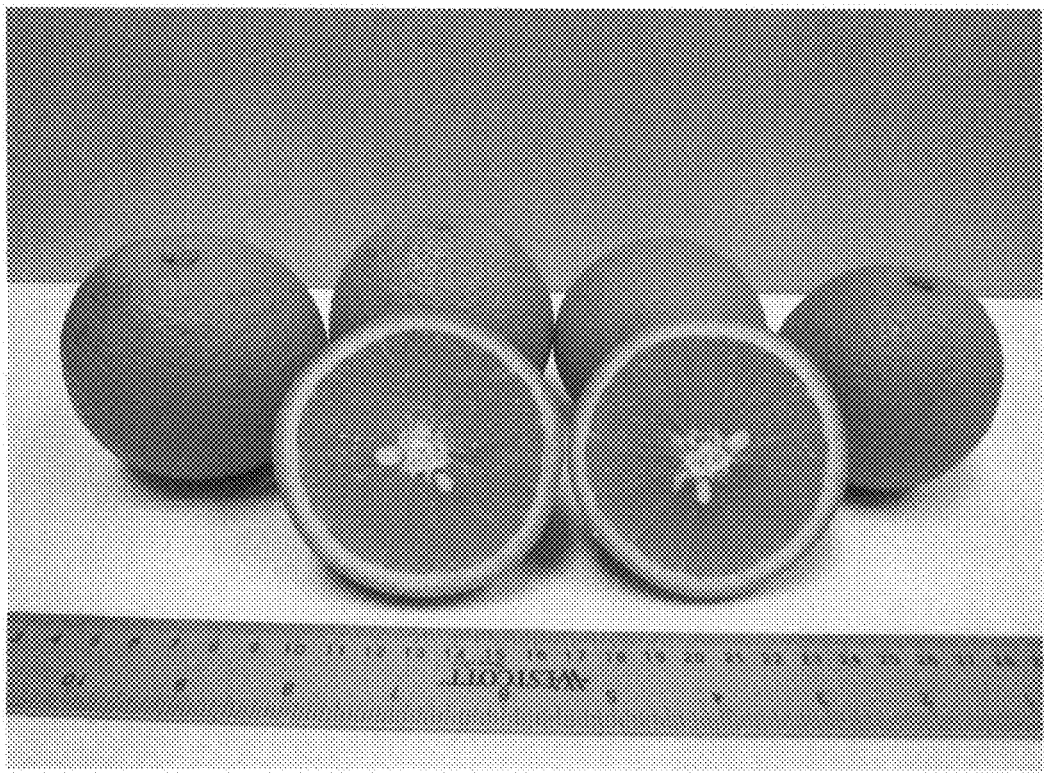
FIGS. 1-3 were taken during the early winter (December 2014) from the same tree.
Figure 2:
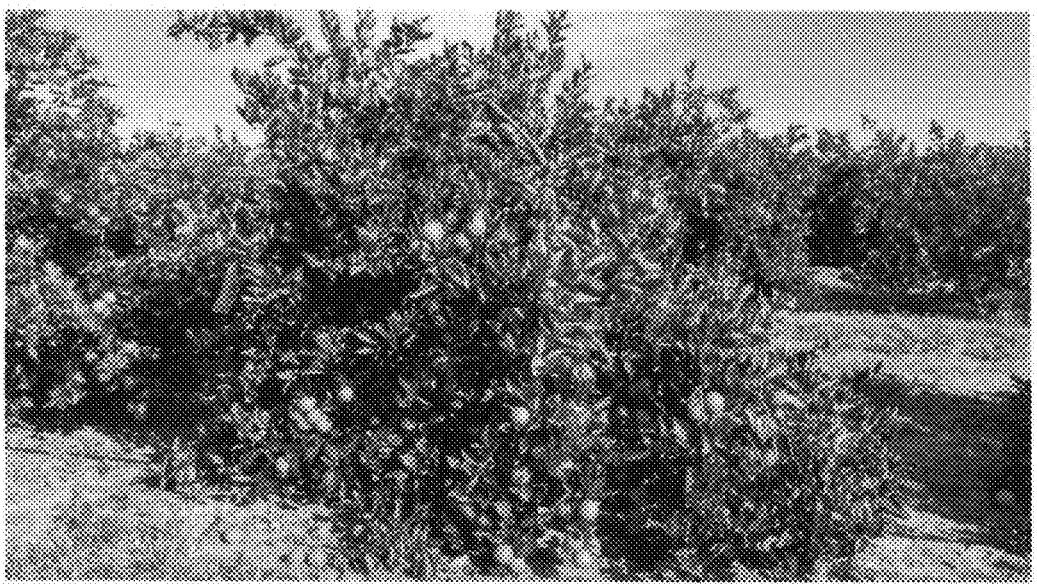
Figure 3:
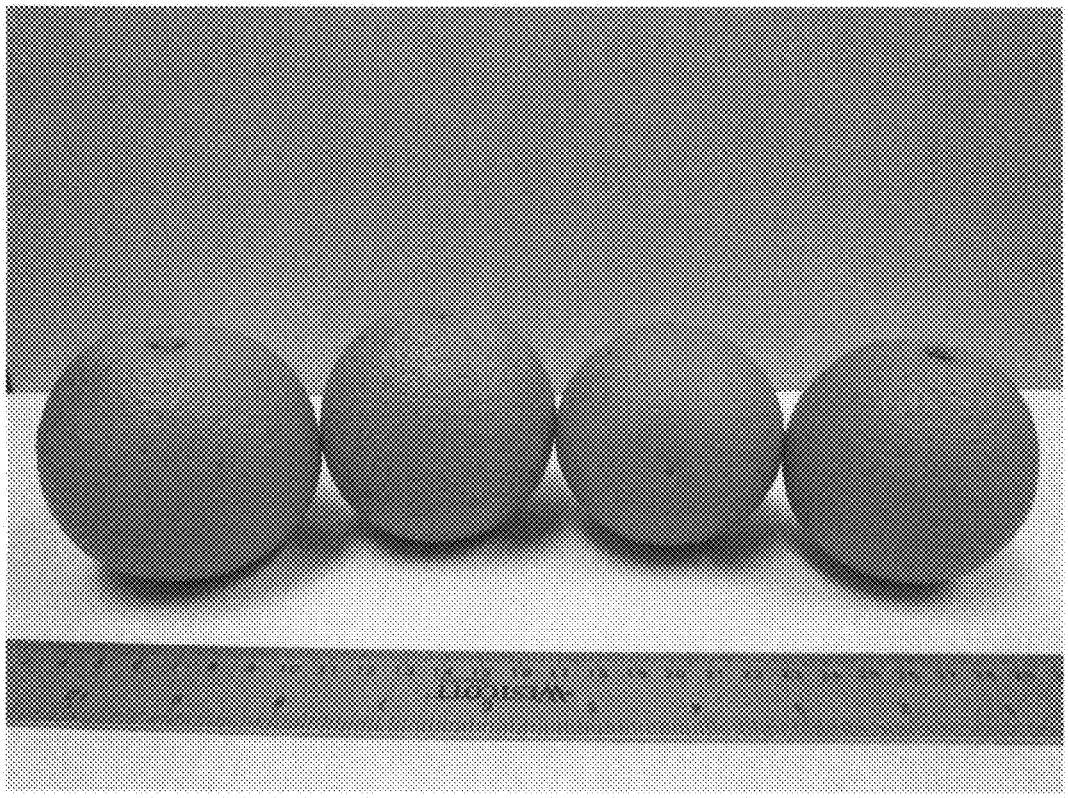

Phenotypic Description of *Citrus sinensis* 'Florida EV1'

The following detailed description sets forth the distinctive characteristics of 'Florida EV1'. The present botanical description is that of 'Florida EV1' grown as a 5-year-old tree growing on 'Rough Lemon' (rootstock) in St. Cloud, Fla. The colors (except those in common terms) are described from The R.H.S. Colour Chart published by The Royal Horticultural Society in London (second edition), in association with the Flower Council of Holland.

Classification:

*Botanical.*—*Citrus sinensis* (putative).

*Common name.*—Sweet orange.

Parentage:

*Female parent.*—'Valencia' sweet orange (unpatented).

*Male parent.*—N/A.

Tree:

*Ploidy.*—Diploid.

*Size.*—Medium.

*Height.*—2.1 meters.

*Tree spread.*—3.5 to 4 meters.

*Vigor.*—Less vigorous than standard 'Valencia'.

*Density.*—Canopies are quite dense.

*Form.*—The tree is obloid shaped with lateral and upright branches growing toward low to medium angles. Branches with multiple fruits exhibit drooping.

*Growth habit.*—Both upright and lateral growth.

Trunk and branches:

*Trunk diameter.*—9.4 cm at 30 cm above the ground on a 5-year-old tree.

*Trunk texture.*—Smooth.

*Trunk bark color.*—RHS 197A (greyed-green); irregularly striated with RHS 146C (yellow-green).

*Crotch angle.*—First crotch forms a 55- to 60-degree angle, middle crotch forms a 30-degree angle.

*Branch length.*—Branches reach 3 meters from the first crotch to the tip of the branch.

*Branch texture.*—Relatively smooth, occasionally with thorns.

*Branch color* (*shoots from previous flush, hardened and 4 to 5 mm in diameter*).—RHS 146A (yellow-green).

Leaves:

*Size* (*lamina average*).—Length: 123 mm. Width: 71.3 mm. L/W ratio: 1.72.

*Thickness.*—Regular and average compare to commercial sweet orange.

*Type.*—Simple.

*Shape.*—Elliptical.

*Apex.*—Retuse.

*Base.*—Acute to sub-obtuse.

*Margin.*—Entire and slightly undulate.

*Surface.*—Upper surface: Glabrous. Lower surface: Medium veins that are pinnately netted.

*Color.*—Upper surface (adaxial): RHS 147A (yellow-green). Lower surface (abaxial): RHS 146B (yellow-green).

*Petiole.*—Shape: Brevipetiolate (shorter than leaf lamina); junction between petiole and lamina is articulate. Width (petiole wing): Very narrow. Shape (petiole wing): Obovate. Length: 15.7 to 23.2 mm. Width: 3.6 to 4.5 mm. Color: RHS 147A (yellow-green).

Flowers and flower buds:

*Type.*—Hermaphroditic.

*Bearing.*—Flowers grow from leaf axillaries and leaf terminals in small clusters, with each flower branch consisting of 5-12 flowers.

*Flower diameter.*—Fully open flower has an average diameter of 46.5 to 47 mm.

*Flower depth.*—Typical flower has an average depth of 20 mm.

*Flower blooming period.*—First bloom observed Feb. 28, 2015. Full bloom observed Mar. 5, 2015.

*Flower bud size.*—Length: Initial visible flower bud is 2.8 mm in length; mature flower bud is 21.4 mm in length. Diameter: Initial visible flower bud is 2.9 mm in diameter; mature flower bud is 10.8 mm in diameter. Shape: Initial visible flower bud has a round ball shape; mature flower bud has an elongated olive shape.

*Color.*—RHS144D (yellow-green) for initial visible flower bud; RHS155B (white) for mature flower bud, with RHS150D (yellow-green) spots distributed at tip of the flower bud.

*Flower petals.*—Shape: Flat, spatula-shaped. Apex shape: Smooth, acute-shaped. Base shape: Even obtuse.

*Color.*—Upper surface RHS155B (white); lower surface RHS155B (white), with RHS150D (yellow-green) spots distributed toward to the petal apex. Margin: Smooth.

*Flower sepal.*—Number: 5 per flower. Shape: Delta-shaped with acute angle at apex. Length: 3.8 mm. Width: 4.4 mm. Apex shape: Triangle-shaped. Margin: Smooth. Color: Upper surface RHS145C (yellow-green); lower surface RHS145A (yellow-green).

*Fragrance.*—Fragrant.

*Flower pedicel.*—Length: 9.0 to 9.4 mm. Diameter: 1.5 to 1.7 mm. Color: RHS144A (yellow-green).

Reproductive organs:

*Fertility.*—Appears self-fertile.

*Stamen length.*—12.5 to 12.7 mm.

*Anther length.*—2.9 mm.

*Anther width.*—1.0 to 1.1 mm.

*Anther color.*—RHS12B (yellow).

*Anther filament length.*—12.8 to 12.9 mm.

*Pollen amount*.—Abundant.
*Pollen color* (*general*).—RHS12A (yellow).
*Pistil number*.—1.
*Pistil length*.—13.1 to 13.2 mm.
*Pistil color*.—RHS2D (yellow).
*Style length*.—9.6 mm.
*Style diameter*.—1.9 to 2.1 mm.
*Style color*.—RHS150C (yellow).
*Ovary shape*.—Oval-shaped.
*Ovary diameter*.—4.5 mm.
*Ovary color*.—RHS144C (yellow-green).

Fruit:

*Size*.—Uniform.
*Tall*.—72.5 to 76 mm on average.
*Width*.—72.5 to 80 mm on average.
*Average weight* (*per individual fruit*).—219.4 grams.
*Shape*.—Round.
*Shape* (*cross-section*).—Round.
*Apex*.—Truncated.
*Apex cavity diameter*.—N/A.
*Base cavity diameter*.—6.3 to 6.5 mm.
*Base*.—No neck, slightly winkled at base.
*Harvesting*.—First harvest around Dec. 10, 2014 (based on season and rootstock); fruit hold well on the tree through January.
*Fruit stem* (*short stem connecting the fruit*).—Length: 9.7 mm. Diameter: 4.0 mm. Color: RHS 197A (greyed-green) with RHS 144B (yellow-green) strip.
*Fruit core*.—Size: 7.0 mm to 11.0 mm. Color: RHS NN155-B (white).

Rind:

*Adherence*.—Adherence between albedo (mesocarp) and flesh (endocarp) is strong and evenly distributed from base to apex.
*Thickness*.—5.0 to 5.8 mm on average.
*Texture*.—Smooth.
*Color*.—Flavedo (epicarp): Ranges between RHS 23A (yellow-orange) to RHS24A (orange). Albedo (mesocarp): RHS 22C (yellow-orange).
*Stylar end*.—Closed.
*Rind oil cell density*.—268 oil cells/square cm.

Flesh:

*Number of segments*.—Average between 13 and 14 segments per fruit.
*Segment walls*.—Medium soft with sufficient strength to maintain integrity as separated.
*Juice*.—Abundant.
*Color*.—Uniformly RHS 23B (yellow-orange).
*Texture*.—Medium soft.
*Vesicles*.—Length: Arranged from 17.8 to 19.6 mm on average. Diameter (thickness): 1.6 to 2.2 mm on average.
*Eating quality as Dec.* 8, 2014.—Soluble solids (average): 11.3 Brix. Acidity (average): 0.71%. Ratio: 15.9.

Seeds:

*Type*.—Polyembryonic.
*Number*.—Ranges from 9 to 10. Occasionally some fruit contain less than 9 seeds.
*Shape*.—Seed shapes are not uniform. Normal seeds are mostly ventricose/swollen-shaped and clavate, club-shaped.
*Size*.—Length: 8.5 to 12.2 mm. Width: 4.2 to 8.1 mm.
*Seed coat color*.—Outer Surface: RHS NN155A (white) and wrinkled. Inner surface: RHS 164C (greyed-orange).
*Cotyledon color*.—RHS NN155B (white).

Disease/insect resistance: No apparent differences from standard 'Valencia'.

What is claimed is:

1. A new and distinct cultivar of sweet orange tree as illustrated and described herein.

* * * * *